United States Patent
Gerster et al.

(10) Patent No.: US 7,799,951 B2
(45) Date of Patent: Sep. 21, 2010

(54) NON-STAINING ANTIDEGRADANTS FOR VULCANIZED ELASTOMERS

(75) Inventors: Michèle Gerster, Binningen (CH); Hans-Rudolf Meier, Riehen (CH); Gerrit Knobloch, Magden (CH); Pierre Rota-Graziosi, Mulhouse (FR)

(73) Assignee: Ciba Corporation, Tarrytown, NY (US)

( * ) Notice: Subject to any disclaimer, the term of this patent is extended or adjusted under 35 U.S.C. 154(b) by 78 days.

(21) Appl. No.: 11/992,925

(22) PCT Filed: Oct. 2, 2006

(86) PCT No.: PCT/EP2006/066953

§ 371 (c)(1), (2), (4) Date: Apr. 1, 2008

(87) PCT Pub. No.: WO2007/042418

PCT Pub. Date: Apr. 19, 2007

(65) Prior Publication Data

US 2009/0227730 A1    Sep. 10, 2009

(30) Foreign Application Priority Data

Oct. 11, 2005    (EP) .................................. 05109439

(51) Int. Cl.
C08K 5/00 (2006.01)
C08K 5/42 (2006.01)
C08K 5/372 (2006.01)
C07C 317/48 (2006.01)
C07C 323/52 (2006.01)

(52) U.S. Cl. ........................ 564/434; 564/440; 524/236; 524/155

(58) Field of Classification Search ................. 524/236, 524/155; 564/434, 440
See application file for complete search history.

(56) References Cited

U.S. PATENT DOCUMENTS

| | | | | |
|---|---|---|---|---|
| 3,000,852 A | 9/1961 | Merz | ........................ | 260/45.9 |
| 3,035,014 A | 5/1962 | Popoff et al. | ............... | 260/45.9 |
| 4,124,565 A * | 11/1978 | Kuczkowski | ................. | 524/236 |
| 6,365,653 B1 | 4/2002 | Meier et al. | .................. | 524/155 |
| 6,797,755 B1 | 9/2004 | Meier et al. | .................. | 524/155 |
| 2002/0006994 A1* | 1/2002 | Laue et al. | ................... | 524/241 |
| 2006/0041045 A1 | 2/2006 | Meier et al. | ................. | 524/155 |

* cited by examiner

Primary Examiner—Kelechi C Egwim
(74) Attorney, Agent, or Firm—Tyler A. Stevenson

(57) ABSTRACT

The instant invention discloses a process for preventing contact discoloration of substrates coming into contact with elastomers and stabilizing elastomers to prevent oxidative, thermal, dynamic, light-induced and/or ozone-induced degradation, which comprises incorporating into the elastomers, or applying to these, at least a compound of the formula (I) wherein $R_1$ is $C_1$-$C_{12}$alkyl, $R_2$ is $C_1$-$C_{12}$alkyl, or $R_1$ and $R_2$ together with the carbon atom to which they are attached form an unsubstituted or with $C_1$-$C_4$alkyl substituted $C_5$-$C_{12}$cycloalkyl ring; $R_3$ is hydrogen or —$CH_2$—$S(O)_m$—$R_5$, $R_4$ and $R_5$ independently of each other are unsubstituted or with cyano substituted $C_5$-$C_{18}$-alkyl; $C_7$-$C_9$phenylalkyl, unsubstituted or with halogen, hydroxyl, cyano or $C_1$-$C_4$alkyl substituted phenyl or naphthyl; benzothiazolyl or —$R_6$—$CO_2$—$R_7$, $R_6$ is $C_1$-$C_{18}$alkylene, $R_7$ is $C_1$-$C_{18}$alkyl, and m is 0, 1 or 2. The instant invention discloses also novel compounds of the formula (I), new mixtures of compounds of the formula (I) and compositions thereof in elastomers.

(I)

$$R_1\!\!\diagdown_{\!\!\!\!\!\!\!\!\!\!\!\!\!\!\!}CH\text{—}N\text{—}\!\!\bigcirc\!\!\text{—}N\text{—}\!\!\bigcirc\!\!\text{—}CH_2\text{—}S(O)_m\text{—}R_4$$

with $R_2$ on the CH, H on both N's, and $R_3$ on the second ring.

15 Claims, No Drawings

NON-STAINING ANTIDEGRADANTS FOR VULCANIZED ELASTOMERS

The present invention relates to a process for preventing contact discoloration of substrates coming into contact with elastomers and stabilizing elastomers to prevent oxidative, thermal, dynamic, or light- and/or ozone-induced degradation, which comprises incorporating into the elastomers, or applying to these, at least one compound of the para- or para- and ortho-thiomethyl-substituted diphenylamine type. Most of these compounds are new.

Rubber products (vulcanizates), like all polymers, are susceptible to oxidative, thermal, dynamic or light-induced degradation. A particular factor causing damage to diene rubber vulcanizates is ozone. Ozone attacks the carbon-carbon double bonds, of which many remain in the rubber (vulcanizate), and, via the mechanism known as ozonolysis, causes damage which is apparent as typical surface cracking, and failure of the rubber product. The damage is particularly serious when the rubber product is under dynamic stress.

To prevent ozone damage, antiozonants selected from the class consisting of para-phenylenediamines are generally added to vulcanizates. These compounds have very good protective action, especially under dynamic conditions, but develop a strong intrinsic color (discoloring) and, as a result of high migration rate, these compounds give severe contact discoloration (staining), i.e. the dye transfers to other substrates/products on direct contact. This means that the stabilizers employed in the prior art cannot be used as stabilizers for rubber products which are free from carbon black or are "non-black", and they are also unsuitable for (black) rubber products which comprise carbon black and are intended for use in direct contact with pale-coloured products.

U.S. Pat. No. 4,124,565 discloses N,N'-disubstituted p-phenylenediamines as antioxidants and anti-ozonants in rubber compounds.

WO-A-01/29126 discloses compositions comprising an elastomer susceptible to oxidative, thermal, dynamic, or light- and/or ozone-induced degradation and, as stabilizer, at least one compound of the S-substituted 4-(3-mercapto/sulfinyl-2-hydroxypropylamino)diphenylamine type, and also to the use of the stabilizers to prevent contact discoloration of substrates coming into contact with elastomers, and as antiozonants for elastomers to prevent oxidative, thermal, dynamic, or light- and/or ozone-induced degradation.

There continues to be a need for color-stable stabilizers which prevent ozone damage to rubber products, in particular to pale-coloured rubber products. There also continues to be a need for stabilizers which, although they may have an intrinsic color, are unable, for example as a result of chemical bonding to the rubber chains, to transfer the color to other products.

It has now been found that compounds of the para or para and ortho thiomethyl-substituted diphenylamine type are particularly suitable for preventing contact discoloration of substrates coming into contact with elastomers and at the same time stabilizing elastomers to prevent oxidative, thermal, dynamic, or light- and/or ozone-induced degradation.

The present invention therefore provides a process for preventing contact discoloration of substrates coming into contact with elastomers and stabilizing elastomers to prevent oxidative, thermal, dynamic, light-induced and/or ozone-induced degradation, which comprises incorporating into the elastomers, or applying to these, at least a compound of the formula I

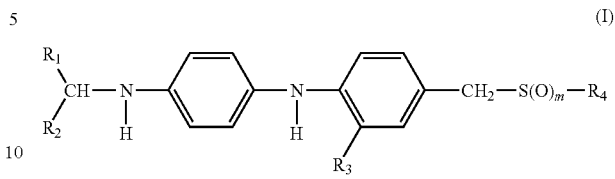

wherein
$R_1$ is $C_1$-$C_{12}$alkyl,
$R_2$ is $C_1$-$C_{12}$alkyl, or $R_1$ and $R_2$ together with the carbon atom to which they are attached form an unsubstituted or with $C_1$-$C_4$alkyl substituted $C_5$-$C_{12}$cycloalkyl ring;
$R_3$ is hydrogen or —$CH_2$—$S(O)_m$—$R_5$,
$R_4$ and $R_5$ independently of each other are unsubstituted or with cyano substituted $C_5$-$C_{18}$-alkyl; $C_7$-$C_9$phenylalkyl, unsubstituted or with halogen, hydroxyl, cyano or $C_1$-$C_4$alkyl substituted phenyl or naphthyl; benzothiazolyl or —$R_6$—$CO_2$—$R_7$,
$R_6$ is $C_1$-$C_{18}$alkylene,
$R_7$ is $C_1$-$C_{18}$alkyl, and
m is 0, 1 or 2.

Alkyl having up to 18 carbon atoms is a branched or unbranched radical, such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, 1,1,3,6,6-pentamethyl-4-heptyl, tridecyl, tetradecyl, pentadecyl, hexadecyl, heptadecyl or octadecyl.

An unsubstituted or with $C_1$-$C_4$alkyl substituted $C_5$-$C_{12}$cycloalkyl ring is for example cyclopentyl, cyclohexyl, cycloheptyl, cyclooctyl, cyclononyl, cyclododecyl, 4-methylcyclohexyl, 4-ethylcyclohexyl, 4-propylcyclohexyl, 4-n-butylcyclohexyl, 4-tert-butylcyclohexyl, 2,4-dimethylcycloheptyl or 3,4-dimethylcyclohexyl. Cyclohexyl is preferred.

A cyano substituted $C_5$-$C_{18}$alkyl is a branched or unbranched radical which contains preferably from 1 to 3, especially 1 or 2, substituents, is, for example, 5-cyanopentyl, 4-cyanopentyl, 3-cyanopentyl, 2-cyanopentyl, 6-cyanohexyl, 5-cyanohexyl, 4-cyanohexyl, 3-cyanohexyl, 2-cyanohexyl, 7-cyanoheptyl, 8-cyanooctyl, 9-cyanononyl, 10-cyanodecyl, 11-cyanoundecyl or 12-cyanododecyl.

$C_7$-$C_9$Phenylalkyl is, for example, benzyl, α-methylbenzyl, α,α-dimethylbenzyl or 2-phenyl-ethyl.

Unsubstituted or with halogen, hydroxyl, cyano or $C_1$-$C_4$alkyl substituted phenyl or naphthyl, which contains preferably from 1 to 3, especially 1 or 2, substituents, is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl, 2,6-diethylphenyl, o-, m- or p-chlorophenyl, o-, m- or p-cyanophenyl; or o-, m- or p-hydroxyphenyl, 2-methylnaphthyl, 1-methylnaphthyl, 4-methylnaphthyl, 6-methylnaphthyl, 4-chloronaphthyl, 6-chloronaphthyl or 6-cyanonaphthyl.

Halogen substitutents will conveniently be chloro, bromo or iodo. Chloro is preferred.

$C_1$-$C_{18}$Alkylene is a branched or unbranched radical, for example methylene, ethylene, propylene, trimethylene, tetramethylene, pentamethylene, hexamethylene, heptamethylene, octamethylene, decamethylene, dodecamethylene, octadecamethylene, 1-methylethylene, 2-methylpropylene or 1-methylmethylene.

An interesting process comprises a compound of the formula I, wherein
$R_1$ is $C_1$-$C_8$alkyl,
$R_2$ is $C_1$-$C_8$alkyl, or $R_1$ and $R_2$ together with the carbon atom to which they are attached form an unsubstituted or with $C_1$-$C_4$alkyl substituted $C_5$-$C_7$cycloalkyl ring;
$R_3$ is hydrogen or —$CH_2$—$S(O)_m$—$R_5$,
$R_4$ and $R_5$ independently of each other are unsubstituted or with cyano substituted $C_5$-$C_{12}$-alkyl; $C_7$-$C_9$phenylalkyl, unsubstituted or with halogen, cyano or $C_1$-$C_4$alkyl substituted phenyl or naphthyl; or —$R_6$—$CO_2$—$R_7$,
$R_6$ is $C_1$-$C_{12}$alkylene,
$R_7$ is $C_1$-$C_{12}$alkyl, and
m is 0, 1 or 2.

A preferred process comprises a compound of the formula I, wherein
$R_3$ is hydrogen or —$CH_2$—$S(O)_m$—$R_5$,
$R_4$ and $R_5$ independently of each other are $C_8$-$C_{12}$alkyl; benzyl, phenyl or —$R_6$—$CO_2$—$R_7$,
$R_6$ is $C_1$-$C_3$alkylene,
$R_7$ is $C_1$-$C_4$alkyl, and
m is 0, 1 or 2.

Preference is also given to a process comprising a compound of the formula I, wherein
$R_1$ is $C_3$-$C_5$alkyl,
$R_2$ is $C_1$-$C_3$alkyl, or $R_1$ and $R_2$ together with the carbon atom to which they are attached form a cyclohexyl ring;
$R_3$ is hydrogen or —$CH_2$—$S(O)_m$—$R_5$,
$R_4$ and $R_5$ independently of each other are $C_8$-$C_{12}$alkyl; benzyl, phenyl or —$R_6$—$CO_2$—$R_7$,
$R_6$ is $C_1$-$C_3$alkylene,
$R_7$ is $C_1$-$C_4$alkyl, and
m is 0, 1 or 2.

The compounds of the formula I are suitable for stabilizing elastomers to prevent oxidative, thermal, dynamic, or light- and/or ozone-induced degradation and to prevent contact discoloration of substrates coming into contact with elastomers.

Rubbers (elastomers) are to be understood as meaning macromolecular materials which after considerable deformation under a small load at room temperature rapidly regain approximately their original shape. See also Hans-Georg Elias, "An Introduction to Polymer Science", Section 12. "Elastomers", pp. 388-393, 1997, VCH Verlagsgesellschaft mbH, Weinheim, Germany or "Ullmann's Encyclopedia of Industrial Chemistry, fifth, completely revised edition, Volume A 23", pp. 221-440 (1993).

Examples of rubbers which may be present in the process of the invention are the following materials:
1. Polymers of conjugated dienes, for example polybutadiene or polyisoprene.
2. Copolymers of mono- and diolefins with one another or with other vinyl monomers, e.g. propylene-isobutylene copolymers, propylene-butadiene copolymers, isobutylene-isoprene copolymers, ethylene-alkyl acrylate copolymers, ethylene-alkyl methacrylate copolymers, ethylene-vinyl acetate copolymers, acrylonitrile-butadiene copolymers, and also terpolymers of ethylene with propylene and with a diene, such as hexadiene, dicyclopentadiene or ethylidenenorbornene.
3. Copolymers of styrene or α-methylstyrene with dienes or with acrylic derivatives, e.g. styrene-butadiene, styrene-butadiene-isoprene, styrene-butadiene-alkyl acrylate and styrene-butadiene-alkyl methacrylate; block copolymers of styrene, e.g. styrene-butadiene-styrene, styrene-isoprene-styrene and styrene-ethylenebutylene-styrene.
4. Halogen-containing polymers, e.g. polychloroprene, chlorinated rubber, chlorinated or brominated copolymers of isobutylene-isoprene (halobutyl rubber), halogenated copolymers of isobutylene and p-methylstyrene.
5. Natural rubber.
6. Aequeous emulsions of natural or synthetic rubbers, e.g. natural rubber latex or latices of carboxylated styrene-butadiene copolymers.

Elastomers of special interest are natural or synthetic rubbers or blends thereof or vulcanizates prepared therefrom.

Preferably, the rubber component is based on highly unsaturated rubbers such as, for example, natural rubber and/or styrene-butadiene rubber and/or butadiene rubber. Representative of the highly unsaturated polymers that can be employed in the practice of this invention are diene rubbers. Such rubbers will ordinarily possess an iodine number of between about 20 to about 450, although highly unsaturated rubbers having a higher or a lower (e.g. of 50-100) iodine number can also be employed. Illustrative of the diene rubbers that can be utilized are polymers based on conjugated dienes such as, for example, 1,3-butadiene; 2-methyl-1,3-butadiene; 1,3-pentadiene; 2,3-dimethyl-1,3-butadiene; and the like, as well as copolymers of such conjugated dienes with monomers such as, for example styrene, α-methylstyrene, acetylene, e.g. vinyl acetylene, acrylonitrile, methacrylate, methyl acrylate, ethyl acrylate, methyl methacrylate, ethyl methacrylate, vinyl acetate, and the like. Preferred highly unsaturated rubbers include natural rubber, cis-polyisoprene, polybutadiene, poly(styrene-butadiene), styrene-isoprene copolymers, isoprene-butadiene copolymers, styrene-isoprene-butadiene tripolymers, polychloroprene, chloro-isobutene-isoprene, nitrile-chloroprene, styrene-chloroprene, and poly(acrylonitrile-butadiene). Moreover, mixtures of two or more highly unsaturated rubbers with elastomers having lesser unsaturation such as EPDM, EPR, butyl or halogenated butyl rubbers are also within the contemplation of the invention.

The elastomers to be protected are preferably vulcanized elastomers. Particular preference is given to vulcanized polymer of conjugated dienes, halogen-containing polydiene vulcanizates, polydiene copolymer vulcanizates, in particular styrene-butadiene copolymer vulcanizates, or ethylene-propylene terpolymer vulcanizates.

The compound of the formula I is usefully added to the elastomer to be stabilized in amounts of from 0.01 to 10%, for example from 0.1 to 5%, preferably from 0.5 to 3.0%, based on the weight of the elastomer to be stabilized.

In addition to the compound of the formula I, the process of the invention may comprise other additives, such as the following:

1. Antioxidants
1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4- methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol, 2,4-didodecylthiomethyl-6-methylphenol, 2-(α,α-dimethylbenzyl)-4,6-dioctylthiomethylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octade-cyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2, 2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6. Alkylidenebis- and polyphenols, for example 2, 2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane, butylated reaction product of p-cresol and dicyclopentadiene.

1.7. O-, N- and S-benzyl compounds, for example 3, 5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3, 5-tris(3,5-di-tert-butyl-4-hydroxy-benzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-triazine, 2-octylmercapto-4,6-bis(3, 5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzyl phosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, evelinlene glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or poly-hydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9- nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene.

1.20. Quinoline derivatives, for example polymerized 2,2,4-trimethyl-1,2-dihydroquinoline, 6-ethoxy-2,2,4-trimethyl-1,2-dihydroquinoline.

2. UV absorbers and light stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-meth-oxycarbonylethyl)phenyl)benzotriazole, 2-(3'-tert-butyl-2'-hydroxy-5'-(2-octyloxycarbonyl-ethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenyl benzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$-]$_2$, where R=3'-tert-butyl-hydroxy-5'-2H-benzotriazol-2-yl phenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-α,α-dimethylbenzyl)phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethyl-butyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2, 2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyl-oxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethyl-phenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl)phosphite, trilauryl phosphite, trioctadecyl phosphite, distearylpentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,4-di-cumylphenyl) pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxyylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-hepta-decylnitrone, N-octadecyl-alpha-hexadecylnitrone, nitrone derived from N,N-dialkylhydroxyl-amine derived from hydrogenated tallow amine.
7. Thiosynergistic compounds, for example thiodipropionic acid dilauryl ester or thiodipropionic acid distearyl ester or compounds of formula IV

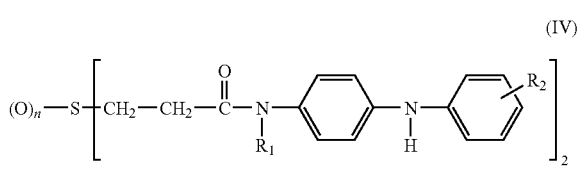

wherein
$R_1$ is hydrogen, $C_1$-$C_{12}$alkyl, cyclohexyl, phenyl or benzyl,
$R_2$ is hydrogen or $C_1$-$C_4$alkyl, and
n is the number 0, 1 or 2.
8. Peroxide scavengers, for example esters of β-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(β-dodecylmercapto)propionate.
9. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.
10. Fillers and reinforcing agents, for example calcium carbonate, silicates, glass fibres, glass beads, talc, kaolin, mica, barium sulfate, metal oxides and hydroxides, carbon black, graphite, wood flour and flours or fibers of other natural products, synthetic fibers
11. Other additives, for example plasticisers, lubricants, emulsifiers, pigments, rheology additives, catalysts, flow-control agents, optical brighteners, flameproofing agents, antistatic agents and blowing agents.
12. Benzofuranones and indolinones, for example those disclosed in U.S. Pat. No. 4,325,863; U.S. Pat. Nos. 4,338,244; 5,175,312; 5,216,052; 5,252,643; DE-A-4316611; DE-A-4316622; DE-A-4316876; EP-A-0589839; EP-A-0591102 or EP-A-1291384 or 3-[4-(2-acetoxyethoxy)phenyl]-5,7-di-tert-butyl benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one or 3-(2-actyl-5-isooctyl phenyl)-5-isoocyl benzofuran-2-one.

A preferred process of the invention comprises, as other additives, one or more components selected from the group consisting of pigments, dyes, fillers, levelling assistants, dispersants, plasticizers, vulcanization activators, vulcanization accelerators, vulcanizers, charge control agents, adhesion promoters, light stabilizers or antioxidants, such as phenolic antioxidants (items 1.1 to 1.18 in the list) or aminic antioxidants (item 1.19 in the list), organic phosphites or phosphonites (item 4 in the list), thiosynergists (item 7 in the list) and/or benzofuranones (item 12 in the list).

An example of the concentrations at which these other additives are added is from 0.01 to 10%, based on the total weight of the elastomer to be stabilized.

The compounds of the formula I, and also, if desired, other additives are incorporated into the rubber in one-step or multi-step, for example during mixing in internal mixers with rams (Banbury), on mixing rolls or in mixing extruders, prior to vulcanization. When added to the rubber, the compounds of the formula I and, if desired, other additives may also be in the form of a masterbatch comprising these, for example at a concentration of from 2.5 to 25% by weight.

The compounds of the formula I and, if desired, other additives may also be added during the production process of synthetic elastomers or during the compounding prior to crosslinking, which may also comprise other components, such as carbon black as filler and/or ex-tender oils.

The compounds of the formula I are partially bonded chemically to polymer chains under processing conditions (mixing, vulcanization, etc.). The compounds of the formula I are resistant to extraction, i.e. they continue to offer good protection after the substrate is subjected to intensive extraction. The loss of compounds of the formula I from the elastomer via migration or extraction is extremely low.

The elastomers stabilized with the compounds of the formula I also show markedly improved and desirable gloss. This means that the surface gloss of the elastomer stabilized according to the invention, after exposure to ozone, is significantly higher than that of an unstabilized elastomer or of an elastomer stabilized in accordance with the prior art.

The compounds of the formula I and, if desired, other additives may be in pure form or en-capsulated in waxes, in oils or in polymers when they are incorporated into the elastomer to be stabilized.

The compounds of the formula I and, if desired, other additives may also be sprayed onto the elastomer to be stabilized. They are capable of diluting other additives (e.g. the conventional additives given above) or melts of these, and they may therefore also be sprayed together with these additives onto the elastomer to be stabilized.

The resultant stabilized elastomers may be used in a wide variety of forms, e.g. ribbons, moulding compositions, profiles, conveyor belts or tyres.

Of special interest are also new mixtures of compounds of the formula I wherein in one compound of the formula I $R_3$ is hydrogen or $C_1$-$C_{12}$alkyl and wherein in the other compound of the formula I $R_3$ is —$CH_2$—S(O)$_m$$R_5$, wherein m is 0, 1 or 2; $R_5$ is unsubstituted or with cyano substituted $C_5$-$C_{18}$-alkyl; $C_7$-$C_9$phenylalkyl, unsubstituted or with halogen, hydroxyl, cyano or $C_1$-$C_4$alkyl substituted phenyl; or —$R_6$—$CO_2$—$R_7$; $R_6$ is $C_1$-$C_{18}$alkylene; and $R_7$ is $C_1$-$C_{18}$alkyl.

The present invention relates therefore to a mixture comprising
a) at least a compound of the formula I

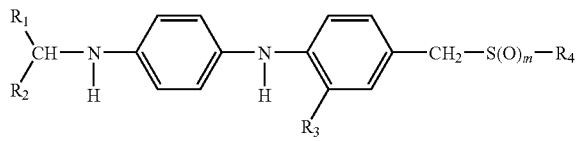

(I)

wherein
$R_1$ is $C_1$-$C_{12}$alkyl,
$R_2$ is $C_1$-$C_{12}$alkyl, or $R_1$ and $R_2$ together with the carbon atom to which they are attached form an unsubstituted or with $C_1$-$C_4$alkyl substituted $C_5$-$C_{12}$cycloalkyl ring;
$R_3$ is hydrogen,
$R_4$ is an unsubstituted or with cyano substituted $C_5$-$C_{18}$alkyl; $C_7$-$C_9$phenylalkyl, unsubstituted or with halogen, hydroxyl, cyano or $C_1$-$C_4$alkyl substituted phenyl or naphthyl; benzothiazolyl or —$R_6$—$CO_2$—$R_7$,
$R_6$ is $C_1$-$C_{18}$alkylene,
$R_7$ is $C_1$-$C_{18}$alkyl, and
m is 0, 1 or 2; and
b) at least a compound of the formula I

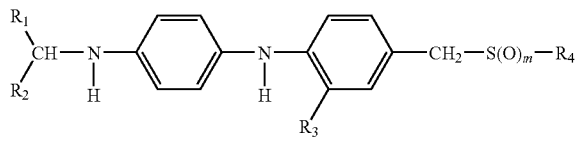

(I)

wherein
$R_1$ is $C_1$-$C_{12}$alkyl,
$R_2$ is $C_1$-$C_{12}$alkyl, or $R_1$ and $R_2$ together with the carbon atom to which they are attached form an unsubstituted or with $C_1$-$C_4$alkyl substituted $C_5$-$C_{12}$cycloalkyl ring;
$R_3$ is —$CH_2$—$S(O)_m$—$R_5$,
$R_4$ and $R_5$ independently of each other are unsubstituted or with cyano substituted $C_5$-$C_{18}$alkyl; $C_7$-$C_9$phenylalkyl, unsubstituted or with halogen, hydroxyl, cyano or $C_1$-$C_4$alkyl substituted phenyl or naphthyl; benzothiazolyl or —$R_6$—$CO_2$—$R_7$,
$R_6$ is $C_1$-$C_{18}$alkylene,
$R_7$ is $C_1$-$C_{18}$alkyl, and
m is 0, 1 or 2.

The preferred radicals for the mixture are the same as those for the process.

Of special interest is a mixture comprising
a) at least a compound of the formula I

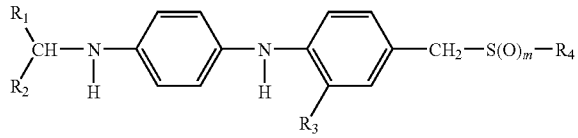

(I)

wherein
$R_1$ is $C_3$-$C_5$alkyl,
$R_2$ is $C_1$-$C_3$alkyl, or $R_1$ and $R_2$ together with the carbon atom to which they are attached form a cyclohexyl ring;
$R_3$ is hydrogen,
$R_4$ is $C_8$-$C_{12}$alkyl, benzyl, phenyl or —$R_6$—$CO_2$—$R_7$,
$R_6$ is $C_1$-$C_3$alkylene,
$R_7$ is $C_1$-$C_4$alkyl, and
m is 0, 1 or 2; and
b) at least a compound of the formula I

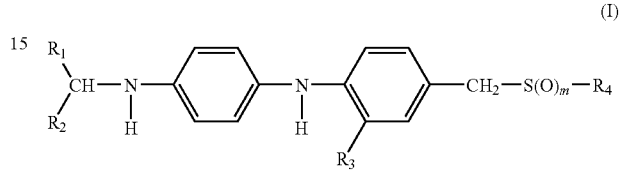

(I)

wherein
$R_1$ is $C_3$-$C_5$alkyl,
$R_2$ is $C_1$-$C_3$alkyl, or $R_1$ and $R_2$ together with the carbon atom to which they are attached form a cyclohexyl ring;
$R_3$ is —$CH_2$—$S(O)_m$—$R_5$,
$R_4$ and $R_5$ independently of each other are $C_8$-$C_{12}$alkyl, benzyl, phenyl or —$R_6$—$CO_2$—$R_7$,
$R_6$ is $C_1$-$C_3$alkylene,
$R_7$ is $C_1$-$C_4$alkyl, and
m is 0, 1 or 2.

The present invention provides also a composition comprising
a) an elastomer susceptible to oxidative, thermal, dynamic, light-induced and/or ozone-induced degradation, and
b) as stabilizer, at least a new mixture of compounds of the formula I as outlined above.

The preferred elastomers are the same as those for the new process. The new composition may comprise in addition to components (a) and (b), further additives. Preferred further additives are the same as those for the new process.

Most of the compounds of the formula I are new. A further embodiment of the present invention is therefore a compound of the formula I

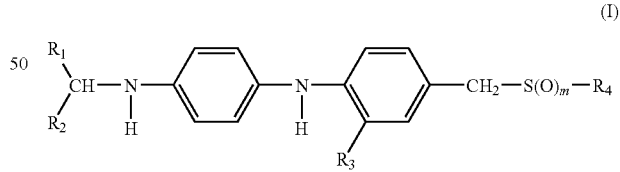

(I)

wherein
$R_1$ is $C_1$-$C_{12}$alkyl,
$R_2$ is $C_1$-$C_{12}$alkyl, or $R_1$ and $R_2$ together with the carbon atom to which they are attached form an unsubstituted or with $C_1$-$C_4$alkyl substituted $C_5$-$C_{12}$cycloalkyl ring;
$R_3$ is hydrogen or —$CH_2$—$S(O)_m$—$R_5$,
$R_4$ and $R_5$ independently of each other are unsubstituted or with cyano substituted $C_5$-$C_{18}$-alkyl; $C_7$-$C_9$phenylalkyl, unsubstituted or with halogen, hydroxyl, cyano or $C_1$-$C_4$alkyl substituted phenyl or naphthyl; benzothiazolyl or —$R_6$—$CO_2$—$R_7$, $R_6$ is $C_1$-$C_{18}$alkylene,
$R_7$ is $C_1$-$C_{18}$alkyl, and
m is 0, 1 or 2; with the proviso that the compounds of the formula Ia

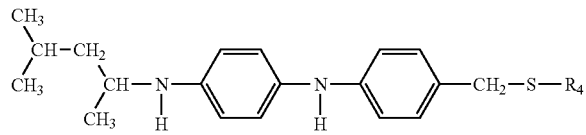

(Ia)

wherein $R_4$ is $C_8$alkyl, $C_{12}$alkyl or phenyl are excluded.

The disclaimer eliminates the three specifically disclosed compounds in U.S. Pat. No. 4,124,565.

Of special interest are new compounds of the formula I, wherein
$R_1$ is $C_3$-$C_5$alkyl,
$R_2$ is $C_1$-$C_3$alkyl, or $R_1$ and $R_2$ together with the carbon atom to which they are attached form a cyclohexyl ring;
$R_3$ is hydrogen or —$CH_2$—$S(O)_m$—$R_5$,
$R_4$ and $R_5$ independently of each other are $C_8$-$C_{12}$alkyl; benzyl, phenyl or —$R_6$—$CO_2$—$R_7$,
$R_6$ is $C_1$-$C_3$alkylene,
$R_7$ is $C_1$-$C_4$alkyl, and
m is 0, 1 or 2; with the proviso that the compounds of the formula Ia

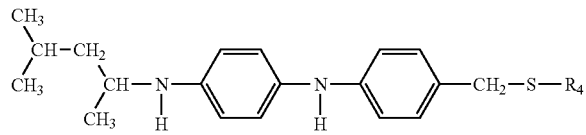

(Ia)

wherein $R_4$ is $C_8$alkyl, $C_{12}$alkyl or phenyl are excluded.

The present invention provides also a composition comprising
  a) an elastomer susceptible to oxidative, thermal, dynamic, light-induced and/or ozone-induced degradation, and
  b) as stabilizer, at least a new compound of the formula I as outlined above.

The preferred elastomers are the same as those for the new process. The new composition may comprise in addition to components (a) and (b), further additives. Preferred further additives are the same as those for the new process.

The preparation of the compounds of the formula I, m is 0, can for example be prepared in analogy to the procedure disclosed in U.S. Pat. No. 4,124,565, Example I, which comprises reacting a compound of the formula IIa

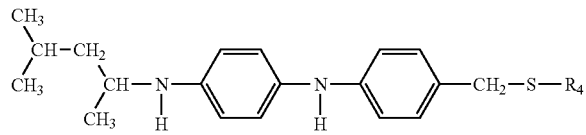

(IIa)

with formalin and an n-dodecanethiol in the presence of ethanol and hydrochloric acid.

We have found that this procedure has the disadvantage that the yield of the product is not very high and that the product contains 32% (GLC) of the starting material [compound of formula IIa] and more than 6% of unreacted n-dodecane thiol (GLC) [see also Example 6b in the experimental part of the instant application].

We have surprisingly found that the yield of the compounds of the formula I, when m is 0, can be drastically improved by using another molar ratio of the starting compounds and/or by using an other solvent, namely a polar, aprotic solvent such as 1,4-dioxane, and/or by using another acid such as e.g. sulfuric acid instead of hydrochloric acid.

The present invention relates therefore also to an improved process for the preparation of the compounds of the formula I

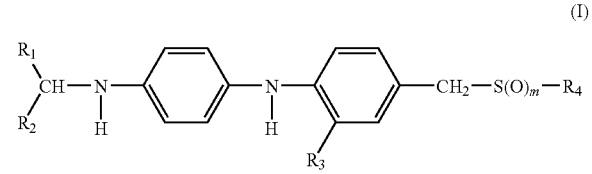

(I)

wherein
$R_1$ is $C_1$-$C_{12}$alkyl,
$R_2$ is $C_1$-$C_{12}$alkyl, or $R_1$ and $R_2$ together with the carbon atom to which they are attached form an unsubstituted or with $C_1$-$C_4$alkyl substituted $C_5$-$C_{12}$cycloalkyl ring;
$R_3$ is hydrogen or —$CH_2$—$S(O)_m$—$R_5$,
$R_4$ and $R_5$ independently of each other are unsubstituted or with cyano substituted $C_5$-$C_{18}$-alkyl; $C_7$-$C_9$phenylalkyl, unsubstituted or with halogen, hydroxyl, cyano or $C_1$-$C_4$alkyl substituted phenyl or naphthyl; benzothiazolyl or —$R_6$—$CO_2$—$R_7$,
$R_6$ is $C_1$-$C_{18}$alkylene,
$R_7$ is $C_1$-$C_{18}$alkyl, and
m is 0; which comprises reacting a compound of the formula II

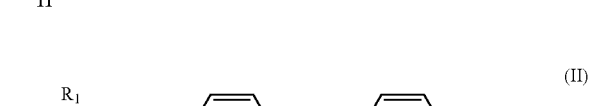

(II)

wherein
$R_1$ is $C_1$-$C_{12}$alkyl,
$R_2$ is $C_1$-$C_{12}$alkyl, or $R_1$ and $R_2$ together with the carbon atom to which they are attached form an unsubstituted or with $C_1$-$C_4$alkyl substituted $C_5$-$C_{12}$cycloalkyl ring; with formaldehyde and a thiol of the formula III and/or IV

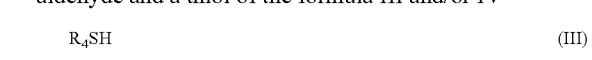  $R_4SH$ (III)

  $R_5SH$ (IV)

wherein
$R_4$ and $R_5$ independently of each other are unsubstituted or with cyano substituted $C_5$-$C_{18}$-alkyl; $C_7$-$C_9$phenylalkyl, unsubstituted or with halogen, hydroxyl, cyano or $C_1$-$C_4$alkyl substituted phenyl or naphthyl; benzothiazolyl or —$R_6$—$CO_2$—$R_7$, $R_6$ is $C_1$-$C_{18}$alkylene, and $R_7$ is $C_1$-$C_{18}$alkyl; in the presence of a solvent and a mineral acid; with the proviso that the compounds of the formula II, III, IV and formaldehyde are not used in equimolar amounts.

The preferred compounds of the formula I, when m is 0, in the improved process for their preparation are the same as outlined above for the process for preventing contact discoloration of substrates coming into contact with elastomers and stabilizing elastomers to prevent oxidative, thermal, dynamic, light-induced and/or ozone-induced degradation.

Preferred solvents are for example alcohols, e.g ethanol; or cyclic ethers, for example tetrahydrofuran or dioxane. Of special interest is 1,4-dioxane.

Depending on the molar amounts of formaldehyde and compounds of the formula III and/or IV used, the electrophilic substitution reaction can lead to a mixture of possible isomeric compounds of the formula I such as only p-substituted, o- and p-substituted and minor amounts of other isomers.

Mineral acids of interest are for example hydrochloric acid, sulfuric acid or phosphoric acid. Of special interest is hydrochloric acid or sulfuric acid, especially sulfuric acid.

Preferably, the mineral acid is used in a concentration of 20-50%, especially 20-30%, for example 30%.

Preferably the thiol of the formula III and/or IV, the formaldehyde and the mineral acid is used in a molar excess of 102-150 mol %, especially 110-125 mol %, for example 115 mol %, in respect to the starting amine (compound of the formula II).

The reaction is carried out preferably at temperatures of from 20 to 120° C., especially from 20 to reflux temperature. Conveniently, the reaction mixture is refluxed for 2 to 6 hours or simply over night.

Preferably the isomeric mixture of the compounds of the formula I, wherein m is 0, prepared according to the improved process is not separated into the pure isomers.

The instant invention relates therefore also to products obtainable by the above new improved process for the preparation of the compounds of the formula I, wherein m is 0.

The compounds of the formula I in which m is 1 (sulfoxides) or m is 2 (sulfones) may be obtained by known methods, for example, from the compounds of the formula I in which m is 0 (thioethers), by oxidation. An example of a suitable and specifically preferred oxidant is hydrogen peroxide.

Oxidation of the thioethers with an oxidant, such as hydrogen peroxide, can also give sulfinyl compounds which, in the case wherein $R_3$ is —$CH_2$—S—$R_5$, and $R_5$ as the above disclosed meaning, have been oxidized at only one sulfur. All conceivable permutations are possible. These mixtures are likewise suitable as good stabilizers for elastomers, to prevent their oxidative, thermal, dynamic, or light- and/or ozone-induced degradation, and/or as stabilizers to prevent contact discoloration of substrates coming into contact with elastomers.

The compounds of the formulae II, III and IV are known from the literature and are in some cases commercially available.

A further embodiment of the present invention is the use of the compounds of the formula I as stabilizers for elastomers to prevent contact discoloration of substrates coming into contact with elastomers and as stabilizers for elastomers to prevent oxidative, thermal, dynamic, light-induced and/or ozone-induced degradation.

The examples below further illustrate the invention. Data in parts or percentages are based on weight. The prepared compounds of the formula I are summarized in Table 1-6.

TABLE 1

Sulfides

| Compound | $R_1$ | $R_2$ | $R_3$ | $R_4$ | m |
|---|---|---|---|---|---|
| 101 | $CH_3$ | $CH_3$ | H | $C_8H_{17}$ | 0 |
| 102 | $CH_3$ | $CH_3$ | H | n-$C_{12}H_{25}$ | 0 |
| 103 | $CH_3$ | $CH_3$ | H | tert-$C_{12}H_{25}$ | 0 |
| 104 | $CH_3$ | $CH_3$ | H | $CH_2CO_2CH_2CH_3$ | 0 |
| 105 | $(CH_3)_2CHCH_2$ | $CH_3$ | H | $C_8H_{17}$ | 0 |
| 106 | $(CH_3)_2CHCH_2$ | $CH_3$ | H | n-$C_{12}H_{25}$ | 0 |
| 107 | $(CH_3)_2CHCH_2$ | $CH_3$ | H | tert-$C_9H_{19}$ | 0 |
| 108 | $(CH_3)_2CHCH_2$ | $CH_3$ | H | tert-$C_{12}H_{19}$ | 0 |
| 109 | $(CH_3)_2CHCH_2$ | $CH_3$ | H | $CH_2CO_2CH_3$ | 0 |
| 110 | $(CH_3)_2CHCH_2$ | $CH_3$ | H | $CH_2$-phenyl | 0 |
| 111 | $(CH_3)_2CHCH_2$ | $CH_3$ | H | phenyl | 0 |
| 112 | n-$C_6H_{13}$ | $CH_3$ | H | n-$C_{12}H_{25}$ | 0 |
| 113 | cyclohexyl | | H | n-$C_{12}H_{25}$ | 0 |
| 114 | $(CH_3)_2CHCH_2$ | $CH_3$ | H | $CH_2CO_2CH_2CH_3$ | 0 |
| 115 | $CH_3$ | $CH_3$ | H | tert-$C_9H_{19}$ | 0 |
| 116 | $CH_3$ | $CH_3$ | H | $CH_2$-phenyl | 0 |
| 117 | $CH_3$ | $CH_3$ | H | tert-$C_8H_{17}$ | 0 |

TABLE 2

Sulfoxides

| Compound | $R_1$ | $R_2$ | $R_3$ | $R_4$ | m |
|---|---|---|---|---|---|
| 201 | $CH_3$ | $CH_3$ | H | $C_8H_{17}$ | 1 |
| 202 | $CH_3$ | $CH_3$ | H | n-$C_{12}H_{25}$ | 1 |
| 203 | $CH_3$ | $CH_3$ | H | tert-$C_{12}H_{25}$ | 1 |
| 204 | $CH_3$ | $CH_3$ | H | $CH_2CO_2CH_2CH_3$ | 1 |
| 205 | $(CH_3)_2CHCH_2$ | $CH_3$ | H | $C_8H_{17}$ | 1 |
| 206 | $(CH_3)_2CHCH_2$ | $CH_3$ | H | n-$C_{12}H_{25}$ | 1 |
| 207 | $(CH_3)_2CHCH_2$ | $CH_3$ | H | tert-$C_9H_{19}$ | 1 |
| 208 | $(CH_3)_2CHCH_2$ | $CH_3$ | H | tert-$C_{12}H_{19}$ | 1 |
| 209 | $(CH_3)_2CHCH_2$ | $CH_3$ | H | $CH_2CO_2CH_3$ | 1 |
| 210 | $(CH_3)_2CHCH_2$ | $CH_3$ | H | $CH_2$-phenyl | 1 |
| 211 | $(CH_3)_2CHCH_2$ | $CH_3$ | H | phenyl | 1 |
| 212 | n-$C_6H_{13}$ | $CH_3$ | H | n-$C_{12}H_{25}$ | 1 |
| 213 | cyclohexyl | | H | n-$C_{12}H_{25}$ | 1 |
| 214 | $(CH_3)_2CHCH_2$ | $CH_3$ | H | $CH_2CO_2CH_2CH_3$ | 1 |
| 215 | $CH_3$ | $CH_3$ | H | tert-$C_9H_{19}$ | 1 |
| 216 | $CH_3$ | $CH_3$ | H | $CH_2$-phenyl | 1 |
| 217 | $CH_3$ | $CH_3$ | H | tert-$C_8H_{17}$ | 1 |

TABLE 3

Bis-sulfides

| Compound | $R_1$ | $R_2$ | $R_3$ | $R_4$ and $R_5$ | m |
|---|---|---|---|---|---|
| 301 | $CH_3$ | $CH_3$ | —$CH_2$—S(O)$_m$—$R_5$ | $C_8H_{17}$ | 0 |
| 302 | $CH_3$ | $CH_3$ | —$CH_2$—S(O)$_m$—$R_5$ | n-$C_{12}H_{25}$ | 0 |
| 303 | $CH_3$ | $CH_3$ | —$CH_2$—S(O)$_m$—$R_5$ | tert-$C_{12}H_{25}$ | 0 |
| 304 | $CH_3$ | $CH_3$ | —$CH_2$—S(O)$_m$—$R_5$ | $CH_2CO_2CH_2CH_3$ | 0 |
| 305 | $(CH_3)_2CHCH_2$ | $CH_3$ | —$CH_2$—S(O)$_m$—$R_5$ | $C_8H_{17}$ | 0 |

TABLE 3-continued

Bis-sulfides

| Compound | $R_1$ | $R_2$ | $R_3$ | $R_4$ and $R_5$ | m |
|---|---|---|---|---|---|
| 306 | $(CH_3)_2CHCH_2$ | $CH_3$ | $-CH_2-S(O)_m-R_5$ | $n\text{-}C_{12}H_{25}$ | 0 |
| 307 | $(CH_3)_2CHCH_2$ | $CH_3$ | $-CH_2-S(O)_m-R_5$ | $tert\text{-}C_9H_{19}$ | 0 |
| 308 | $(CH_3)_2CHCH_2$ | $CH_3$ | $-CH_2-S(O)_m-R_5$ | $tert\text{-}C_{12}H_{19}$ | 0 |
| 309 | $(CH_3)_2CHCH_2$ | $CH_3$ | $-CH_2-S(O)_m-R_5$ | $CH_2CO_2CH_3$ | 0 |
| 310 | $(CH_3)_2CHCH_2$ | $CH_3$ | $-CH_2-S(O)_m-R_5$ | $CH_2$-phenyl | 0 |
| 311 | $(CH_3)_2CHCH_2$ | $CH_3$ | $-CH_2-S(O)_m-R_5$ | phenyl | 0 |
| 312 | $n\text{-}C_6H_{13}$ | $CH_3$ | $-CH_2-S(O)_m-R_5$ | $n\text{-}C_{12}H_{25}$ | 0 |
| 313 | cyclohexyl | | $-CH_2-S(O)_m-R_5$ | $n\text{-}C_{12}H_{25}$ | 0 |
| 314 | $(CH_3)_2CHCH_2$ | $CH_3$ | $-CH_2-S(O)_m-R_5$ | $CH_2CO_2CH_2CH_3$ | 0 |
| 315 | $CH_3$ | $CH_3$ | $-CH_2-S(O)_m-R_5$ | $tert\text{-}C_9H_{19}$ | 0 |
| 316 | $CH_3$ | $CH_3$ | $-CH_2-S(O)_m-R_5$ | $CH_2$-phenyl | 0 |
| 317 | $CH_3$ | $CH_3$ | $-CH_2-S(O)_m-R_5$ | $tert\text{-}C_8H_{17}$ | 0 |

TABLE 4

Bis-sulfoxides

| Compound | $R_1$ | $R_2$ | $R_3$ | $R_4$ and $R_5$ | m |
|---|---|---|---|---|---|
| 401 | $CH_3$ | $CH_3$ | $-CH_2-S(O)_m-R_5$ | $C_8H_{17}$ | 1 |
| 402 | $CH_3$ | $CH_3$ | $-CH_2-S(O)_m-R_5$ | $n\text{-}C_{12}H_{25}$ | 1 |
| 403 | $CH_3$ | $CH_3$ | $-CH_2-S(O)_m-R_5$ | $tert\text{-}C_{12}H_{25}$ | 1 |
| 404 | $CH_3$ | $CH_3$ | $-CH_2-S(O)_m-R_5$ | $CH_2CO_2CH_2CH_3$ | 1 |
| 405 | $(CH_3)_2CHCH_2$ | $CH_3$ | $-CH_2-S(O)_m-R_5$ | $C_8H_{17}$ | 1 |
| 406 | $(CH_3)_2CHCH_2$ | $CH_3$ | $-CH_2-S(O)_m-R_5$ | $n\text{-}C_{12}H_{25}$ | 1 |
| 407 | $(CH_3)_2CHCH_2$ | $CH_3$ | $-CH_2-S(O)_m-R_5$ | $tert\text{-}C_9H_{19}$ | 1 |
| 408 | $(CH_3)_2CHCH_2$ | $CH_3$ | $-CH_2-S(O)_m-R_5$ | $tert\text{-}C_{12}H_{19}$ | 1 |
| 409 | $(CH_3)_2CHCH_2$ | $CH_3$ | $-CH_2-S(O)_m-R_5$ | $CH_2CO_2CH_3$ | 1 |
| 410 | $(CH_3)_2CHCH_2$ | $CH_3$ | $-CH_2-S(O)_m-R_5$ | $CH_2$-phenyl | 1 |
| 411 | $(CH_3)_2CHCH_2$ | $CH_3$ | $-CH_2-S(O)_m-R_5$ | phenyl | 1 |
| 412 | $n\text{-}C_6H_{13}$ | $CH_3$ | $-CH_2-S(O)_m-R_5$ | $n\text{-}C_{12}H_{25}$ | 1 |
| 413 | cyclohexyl | | $-CH_2-S(O)_m-R_5$ | $n\text{-}C_{12}H_{25}$ | 1 |
| 414 | $(CH_3)_2CHCH_2$ | $CH_3$ | $-CH_2-S(O)_m-R_5$ | $CH_2CO_2CH_2CH_3$ | 1 |
| 415 | $CH_3$ | $CH_3$ | $-CH_2-S(O)_m-R_5$ | $tert\text{-}C_9H_{19}$ | 1 |
| 416 | $CH_3$ | $CH_3$ | $-CH_2-S(O)_m-R_5$ | $CH_2$-phenyl | 1 |
| 417 | $CH_3$ | $CH_3$ | $-CH_2-S(O)_m-R_5$ | $tert\text{-}C_8H_{17}$ | 1 |

TABLE 5

Sulfones

| Compound | $R_1$ | $R_2$ | $R_3$ | $R_4$ | m |
|---|---|---|---|---|---|
| 501 | $CH_3$ | $CH_3$ | H | $C_8H_{17}$ | 2 |
| 502 | $CH_3$ | $CH_3$ | H | $n\text{-}C_{12}H_{25}$ | 2 |
| 503 | $CH_3$ | $CH_3$ | H | $tert\text{-}C_{12}H_{25}$ | 2 |
| 504 | $CH_3$ | $CH_3$ | H | $CH_2CO_2CH_2CH_3$ | 2 |
| 505 | $(CH_3)_2CHCH_2$ | $CH_3$ | H | $C_8H_{17}$ | 2 |
| 506 | $(CH_3)_2CHCH_2$ | $CH_3$ | H | $n\text{-}C_{12}H_{25}$ | 2 |
| 507 | $(CH_3)_2CHCH_2$ | $CH_3$ | H | $tert\text{-}C_9H_{19}$ | 2 |
| 508 | $(CH_3)_2CHCH_2$ | $CH_3$ | H | $tert\text{-}C_{12}H_{19}$ | 2 |
| 509 | $(CH_3)_2CHCH_2$ | $CH_3$ | H | $CH_2CO_2CH_3$ | 2 |
| 510 | $(CH_3)_2CHCH_2$ | $CH_3$ | H | $CH_2$-phenyl | 2 |
| 511 | $(CH_3)_2CHCH_2$ | $CH_3$ | H | phenyl | 2 |
| 512 | $n\text{-}C_6H_{13}$ | $CH_3$ | H | $n\text{-}C_{12}H_{25}$ | 2 |
| 513 | cyclohexyl | | H | $n\text{-}C_{12}H_{25}$ | 2 |
| 514 | $(CH_3)_2CHCH_2$ | $CH_3$ | H | $CH_2CO_2CH_2CH_3$ | 2 |
| 515 | $CH_3$ | $CH_3$ | H | $tert\text{-}C_9H_{19}$ | 2 |
| 516 | $CH_3$ | $CH_3$ | H | $CH_2$-phenyl | 2 |
| 517 | $CH_3$ | $CH_3$ | H | $tert\text{-}C_8H_{17}$ | 2 |

TABLE 6

Bis-sulfones

| Compound | $R_1$ | $R_2$ | $R_3$ | $R_4$ and $R_5$ | m |
|---|---|---|---|---|---|
| 601 | $CH_3$ | $CH_3$ | $-CH_2-S(O)_m-R_5$ | $C_8H_{17}$ | 2 |
| 602 | $CH_3$ | $CH_3$ | $-CH_2-S(O)_m-R_5$ | $n\text{-}C_{12}H_{25}$ | 2 |
| 603 | $CH_3$ | $CH_3$ | $-CH_2-S(O)_m-R_5$ | $tert\text{-}C_{12}H_{25}$ | 2 |
| 604 | $CH_3$ | $CH_3$ | $-CH_2-S(O)_m-R_5$ | $CH_2CO_2CH_2CH_3$ | 2 |
| 605 | $(CH_3)_2CHCH_2$ | $CH_3$ | $-CH_2-S(O)_m-R_5$ | $C_8H_{17}$ | 2 |
| 606 | $(CH_3)_2CHCH_2$ | $CH_3$ | $-CH_2-S(O)_m-R_5$ | $n\text{-}C_{12}H_{25}$ | 2 |
| 607 | $(CH_3)_2CHCH_2$ | $CH_3$ | $-CH_2-S(O)_m-R_5$ | $tert\text{-}C_9H_{19}$ | 2 |
| 608 | $(CH_3)_2CHCH_2$ | $CH_3$ | $-CH_2-S(O)_m-R_5$ | $tert\text{-}C_{12}H_{19}$ | 2 |

TABLE 6-continued

Bis-sulfones

| Compound | $R_1$ | $R_2$ | $R_3$ | $R_4$ and $R_5$ | m |
|---|---|---|---|---|---|
| 609 | $(CH_3)_2CHCH_2$ | $CH_3$ | $-CH_2-S(O)_m-R_5$ | $CH_2CO_2CH_3$ | 2 |
| 610 | $(CH_3)_2CHCH_2$ | $CH_3$ | $-CH_2-S(O)_m-R_5$ | $CH_2$-phenyl | 2 |
| 611 | $(CH_3)_2CHCH_2$ | $CH_3$ | $-CH_2-S(O)_m-R_5$ | phenyl | 2 |
| 612 | $n-C_6H_{13}$ | $CH_3$ | $-CH_2-S(O)_m-R_5$ | $n-C_{12}H_{25}$ | 2 |
| 613 | cyclohexyl | | $-CH_2-S(O)_m-R_5$ | $n-C_{12}H_{25}$ | 2 |
| 614 | $(CH_3)_2CHCH_2$ | $CH_3$ | $-CH_2-S(O)_m-R_5$ | $CH_2CO_2CH_2CH_3$ | 2 |
| 615 | $CH_3$ | $CH_3$ | $-CH_2-S(O)_m-R_5$ | tert-$C_9H_{19}$ | 2 |
| 616 | $CH_3$ | $CH_3$ | $-CH_2-S(O)_m-R_5$ | $CH_2$-phenyl | 2 |
| 617 | $CH_3$ | $CH_3$ | $-CH_2-S(O)_m-R_5$ | tert-$C_8H_{17}$ | 2 |

EXAMPLE 1

Preparation of Compound 101 (Table 1)

18.08 g (80 mmol) of N-isopropyl-4-phenylaminoaniline, 13.5 g (92 mmol) of octanethiol, 6.9 ml (92 mmol) of formaldehyde (36.5%), 40 ml of methanol and 15.2 g (184 mmol) of concentrated HCl are mixed and heated under reflux for 3 hours. After cooling, the reaction mixture is brought to a pH of 9 with 10% sodium hydroxide solution. The reaction mixture is extracted with ethyl acetate. The organic phases are separated, washed with water, combined, dried over sodium sulfate and evaporated to yield 30.3 g (98%) of the compound 101 as a dark oil. The crude product can be further purified by flash chromatography on silica using a mixture of ethyl acetate and hexane as eluent. $^1$H- and $^{13}$C-NMR-spectra are in agreement with compound 101. MS (Cl): 385 (MH$^+$).

EXAMPLE 2

Preparation of Compound 102 (Table 1)

22.63 g (100 mmol) of N-isopropyl-4-phenylaminoaniline are dissolved in 50 ml of 1,4-di-oxane. Then a mixture of 11.3 g (115 mmol) of concentrated sulfuric acid and 26.3 ml of distilled water is added. By means of a dropping funnel 23.3 g (115 mmol) of dodecanethiol, 8.6 ml (115 mmol) of formaldehyde (36.5%) are added and the mixture is heated under reflux for 6 hours at 88° C. After cooling, the reaction mixture is brought to a pH of 9 with 10% sodium hydroxide solution. The reaction mixture is extracted with ethyl acetate. The organic phases are separated, washed with water, combined, dried over sodium sulfate and evaporated to yield 30.5 g (69%) of the compound 102 as a dark oil. MS (Cl): 441 (MH$^+$).

EXAMPLE 3

Preparation of Compound 103 (Table 1)

In analogy to Example 1, a mixture of 30.8 g (136 mmol) of N-isopropyl-4-phenylamino-aniline, 28.4 g (136 mmol) of tert-dodecanethiol, 11.2 g of formaldehyde (36.5%), 100 ml of ethanol and 27.2 g (272 mmol) of concentrated HCl are mixed and stirred for 2 hours at 25° C. and then heated under reflux for 3 hours. Standard work-up as outlined in Example 1 yields 41.1 g (69%) of compound 103 as a brown liquid. The spectroscopic properties are in agreement with compound 103.

EXAMPLE 4

Preparation of Compound 104 (Table 1)

20.5 g (90 mmol) of N-isopropyl-4-phenylaminoaniline, 10.8 g (90 mmol) of ethyl thioglycolate, 7.44 g of formaldehyde (36.5%), 80 ml of ethanol and 18.1 g (180 mmol) of concentrated HCl are mixed and stirred for 2 hours at 25° C. and then heated under reflux for 3 hours. Standard work-up as outlined in Example 1 yields after filtration through silica 40 g (100%) of compound 104 as a brown liquid. MS (Cl): 359 (MH$^+$).

EXAMPLE 5

Preparation of Compound 105 (Table 1)

a) HCl/Ethanol Method

To a mixture of 27.0 g (184 mmol) of octanethiol, 13.8 ml (184 mmol) of formaldehyde (36.5%) and 30 ml of ethanol, a mixture of 43.0 g (160 mmol) of N-(4-methyl-2-pentyl)-4-phenyl-aminoaniline, 50 ml of ethanol and 22.8 g (276 mmol) of concentrated HCl is added at 25° C. The reaction mixture stirred for 2 hours at 25° C. and then heated under reflux for 22 hours. Standard work-up as outlined in Example 1 yields 67.5 g (99%) of compound 105 as a dark oil. MS (Cl): 427 (MH$^+$).

b) Sulfuric Acid/Dioxane Method

To a mixture of 21.5 g (80 mmol) of N-(4-methyl-2-pentyl)-4-phenyl-aminoaniline, 40 ml of 1,4-dioxane, 9.0 g (92 mmol) of concentrated sulfuric acid and 21 ml of distilled water, a mixture of 13.5 g (92 mmol) of octanethiol and 6.9 ml (92 mmol) of formaldehyde (36.5%) is added and then the reaction mixture is heated under reflux for 3 hours. Standard work-up as outlined in Example 1 yields 34.0 g (100%) of compound 105 as a dark oil. Its spectroscopic properties are in agreement with compound 105.

EXAMPLE 6

Preparation of Compound 106 (Table 1)

a) HCl/ethanol Method [115 mol % n-dodecanethiol, 115 mol % formaldehyde, 100 mol % N-(4-methyl-2-pentyl)-4-phenyl-aminoaniline]

To a mixture of 9.3 g (46 mmol) of dodecanethiol, 3.5 ml (46 mmol) of formaldehyde (36.5%) and 12 ml of ethanol, a mixture of 10.7 g (40 mmol) of N-(4-methyl-2-pentyl)-4-phenyl-aminoaniline, 8 ml of ethanol and 6.7 g (80 mmol) of concentrated HCl is added at 25° C. The reaction mixture is stirred for 2 hours at 25° C. and then heated under reflux for 22 hours. Standard work-up as outlined in Example 1 yields 20 g (~100%) of compound 106 as a dark oil. MS (Cl): 483 (MH$^+$). Purity according to GLC: 48%.

b) HCl/Ethanol Method According to U.S. Pat. No. 4,124,565 (Example I, Compound 7) [Equimolar Amounts of Components]

Following exactly the procedure of Example I in U.S. Pat. No. 4,124,565 with the indicated amounts and reaction conditions leads to 97.7 g (~100%) of compound 106 as a dark oil with an assay of only 29% (GLC). The raw material contains 32% (GLC) of the starting material [N-(4-methyl-2-pentyl)-phenylamino-aniline] and more than 6% of unreacted n-dodecanethiol (GLC).

c) Sulfuric Acid/Dioxane Method

To a mixture of 21.5 g (80 mmol) of N-(4-methyl-2-pentyl)-4-phenyl-aminoaniline, 40 ml of 1,4-dioxane, 9.0 g (92 mmol) of concentrated sulfuric acid and 21 ml of distilled water, a mixture of 18.6 g (92 mmol) of n-dodecanethiol and 6.9 ml (92 mmol) of formaldehyde (36.5%) is added at 25° C. The reaction mixture is then heated under reflux for 3 hours. Standard work-up as outlined in Example 1 yields 40 g (~100%) of compound 106 as a dark oil. The spectroscopic properties are in agreement with compound 106. Purity according to GLC: 85%.

d) Sulfuric Acid/Dioxane Method

To 1342 g (5 mol) of N-(4-methyl-2-pentyl)-4-phenylaminoaniline in 2.5 l of 1,4-dioxane is added at 38° C. 1880 g (5.75 mol) of 30% sulfuric acid. To this solution a mixture of 480 g (5.75 mol) of 36% formaldehyde solution and 1164 g (5.75 mol) of n-dodecanethiol is added at 43° C. The reaction mixture is heated to 93° C. at reflux for 4 hours. Then 2267 g of 30% aqueous NaOH is added at 88° C. The two phases are separated and the organic phase is diluted with 2 l of toluene. After washing with 2 l portions of water, the organic phase is filtered and the solvent removed by distillation. Drying at 90° C./0.1 mbar gives 2427 g (100%) of compound 106 as a dark oil. Purity: 91.2% (GLC, area percent); starting compound [N-(4-methyl-2-pentyl)-phenylamino-aniline] less than 1%.

e) Sulfuric Acid/Ethanol Method

To a mixture of 21.5 g (80 mmol) of N-(4-methyl-2-pentyl)-4-phenyl-aminoaniline, 40 ml of ethanol, 11.8 g (120 mmol) of concentrated sulfuric acid and 27.5 ml of distilled water, a mixture of 18.6 g (92 mmol) of n-dodecanethiol and 6.9 ml (92 mmol) of formaldehyde (36.5%) is added at 25° C. The reaction mixture is then heated under reflux for 4 hours. Standard work-up as outlined in Example 1 yields 39.5 g (~100%) of compound 106 as a dark oil. Its spectroscopic properties are in agreement with compound. Purity according to GLC: 83%.

f) HCl/Dioxane Method

To a mixture of 21.5 g (80 mmol) of N-(4-methyl-2-pentyl)-4-phenyl-aminoaniline, 40 ml of 1,4-dioxane, 7.67 ml (92 mmol) of concentrated HCl, a mixture of 18.6 g (92 mmol) of n-dodecanethiol and 6.9 ml (92 mmol) of formaldehyde (36.5%) is added at 25° C. The reaction mixture is then heated under reflux for 5 hours. Standard work-up as outlined in Example 1 yields 39.9 g (~100%) of compound 106 as a dark oil. Its spectroscopic properties are in agreement with compound 106. Purity according to GLC: 77%.

EXAMPLE 7

Preparation of Compound 107 (Table 1)

To a mixture of 43.0 g (160 mmol) of N-(4-methyl-2-pentyl)-4-phenylaminoaniline, 80 ml of 1,4-dioxane, 18.0 g (184 mmol) of concentrated sulfuric acid and 42 ml of distilled water, a mixture of 29.5 g (184 mmol) of tert-nonyl mercaptan and 13.8 ml (184 mmol) of formaldehyde (36.5%) is added at 25° C. The reaction mixture is heated under reflux for 6 hours. Standard work-up as outlined in Example 1 yields 61.9 g (88%) of compound 107 as a dark oil. MS (Cl): 441 (MH$^+$).

EXAMPLE 8

Preparation of Compound 108 (Table 1)

To a mixture of 43.0 g (160 mmol) of N-(4-methyl-2-pentyl)-4-phenyl-aminoaniline, 80 ml of 1,4-dioxane, 9.0 g (92 mmol) of concentrated sulfuric acid and 21 ml of distilled water, a mixture of 18.6 g (92 mmol) of tert-dodecyl mercaptan and 6.9 ml (92 mmol) of formaldehyde (36.5%) is added at 25° C. The reaction mixture stirred for 2 hours at 25° C. and then heated under reflux for 22 hours. Standard work-up as outlined in Example 1 yields 40 g (~100%) of compound 108 as a dark oil. MS (Cl): 483 (MH$^+$).

EXAMPLE 9

Preparation of Compound 109 (Table 1)

To a mixture of 19.5 g (184 mmol) of methyl thioglycolate and 13.8 ml (184 mmol) of formaldehyde (36.5%), a mixture of 42.9 g (160 mmol) of N-(4-methyl-2-pentyl)-4-phenyl-amino-aniline, 80 ml of methanol and 26.6 g (320 mmol) of concentrated HCl is added at 25° C. The reaction mixture stirred for 2 hours at 25° C. and then heated under reflux for 22 hours. Standard work-up as outlined in Example 1 yields 79.7 g (>100%) of compound 109 as a dark viscous oil. MS (Cl): 387 (MH$^+$).

EXAMPLE 10

Preparation of Compound 110 (Table 1)

To a mixture of 26.9 g (100 mmol) of N-(4-methyl-2-pentyl)-4-phenylaminoaniline, 40 ml of 1,4-dioxane, 9.8 g (100 mmol) of concentrated sulfuric acid and 21 ml of distilled water, a mixture of 12.4 g (100 mmol) of benzylmercaptan and 8.0 ml (100 mmol) of formaldehyde (36.5%) is added at 25° C. The reaction mixture is heated under reflux for 16 hours at 88° C. Standard work-up as outlined in Example 1 yields 37.4 g (92%) of compound 110 as a dark oil. MS (Cl): 405 (MH$^+$).

EXAMPLE 11

Preparation of Compound 111 (Table 1)

To a mixture of 26.9 g (100 mmol) of N-(4-methyl-2-pentyl)-4-phenylaminoaniline, 40 ml of 1,4-dioxane, 9.8 g (100 mmol) of concentrated sulfuric acid and 21 ml of distilled water, a mixture of 11.0 g (100 mmol) of thiophenol and 8.0 ml (100 mmol) of formaldehyde (36.5%) is added at 25° C. The reaction mixture is heated under reflux for 6 hours at 88° C. Standard work-up as outlined in Example 1 yields 37.4 g (92%) of compound III as a viscous oil. The purified compound III crystallizes. Melting point 51-53° C. MS (Cl): 391 (MH$^+$).

EXAMPLE 12

Preparation of Compound 112 (Table 1)

To a mixture of 29.7 g (100 mmol) of N-(2-octyl)-4-phenylaminoaniline, 50 ml of 1,4-dioxane, 11.3 g (115 mmol) of concentrated sulfuric acid and 26.3 g of distilled water, a mixture of 23.3 g (115 mmol) of n-dodecanethiol and 8.6 ml (115 mmol) of formaldehyde (36.5%) is added at 25° C. The reaction mixture is stirred for 2 hours at 25° C. and then heated under reflux for 22 hours at 88° C. Standard work-up as outlined in Example 1 yields 51 g (100%) of compound 112 as a dark oil. MS (Cl): 511 (MH$^+$).

EXAMPLE 13

Preparation of Compound 113 (Table 1)

To a mixture of 26.5 g (100 mmol) of N-cyclohexyl-4-phenylaminoaniline, 50 ml of 1,4-dioxane, 11.3 g (115 mmol) of concentrated sulfuric acid and 26.3 g of distilled water, a mixture of 23.3 g (115 mmol) of n-dodecanethiol and 8.6 ml (115 mmol) of formaldehyde (36.5%) is added at 25° C. The reaction mixture is stirred for 2 hours at 25° C. and then heated under reflux for 22 hours at 88° C. Standard work-up as outlined in Example 1 yields 46.3 g (97%) of compound 113 as a dark oil. MS (Cl): 481 (MH$^+$).

In analogy to Example 13 are prepared from the corresponding starting materials compounds 114 [N-(4-methyl-2-pentyl)-4-phenylaminoaniline and ethyl thioglycolate instead of N-cyclohexyl-4-phenylaminoaniline and n-dodecanethiol], 115 [N-isopropyl-4-phenylaminoaniline and tert-nonyl mercaptan instead of N-cyclohexyl-4-phenylaminoaniline and n-dodecanethiol], 116 [N-isopropyl-4-phenylaminoaniline and benzylmercaptan instead of N-cyclohexyl-4-phenylaminoaniline and n-dodecanethiol]; and 117 [N-isopropyl-4-phenylaminoaniline and tert-octyl mercaptan instead of N-cyclohexyl-4-phenylaminoaniline and n-dodecanethiol].

EXAMPLE 14

Preparation of Compound 201 (Table 2)

To a mixture of 6.03 g (19 mmol) of $H_2O_2$-urea adduct (30% $H_2O_2$) and 65 ml of ethanol, a solution of 9.2 g (24 mmol) of sulfide [compound 101 prepared according to Example 1] in 25 ml of ethanol is added at 40° C. The reaction mixture is stirred for 4 hours at 40° C. The solvent is evaporated and the formed urea separated by addition of methylene chloride and filtration. Evaporation of the solvent from the filtrate and chromatography on silica with ethyl acetate/hexane 1:1) yields 8.8 g (92%) of compound 201 as a yellow solid, m.p 104° C. MS (Cl): 373 (MH$^+$).

EXAMPLE 15

Preparation of Compound 203 (Table 2)

To a mixture of 5.4 g (17 mmol) of $H_2O_2$-urea adduct (30% $H_2O_2$) and 60 ml of ethanol, is added a solution of 9.2 g (22 mmol) of sulfide [compound 103 prepared according to Example 3] in 30 ml of ethanol. The reaction mixture is stirred for 4 hours at 40° C. Work-up as described in Example 14 and chromatography on silica with ethyl acetate/hexane 1:1 gives 7.4 g (92%) of compound 203 as a brown resin.

EXAMPLE 16

Preparation of Compound 204 (Table 2)

To a mixture of 4.1 g (13 mmol) of $H_2O_2$-urea adduct (30% $H_2O_2$) and 45 ml ethanol, a solution of 5.8 g (16 mmol) of sulfide [compound 104 prepared according to Example 4] in 25 ml of ethanol is added. The reaction mixture is stirred for 4 hours at 40° C. The solvent is evaporated and the urea is separated by addition of methylene chloride and filtration. Evaporation of the solvent from the filtrate and chromatography on silica with ethyl acetate/hexane 3:1 yields 4.2 g (69%) of compound 204 as a yellow brown resin.

EXAMPLE 17

Preparation of Compound 205 (Table 2)

To a mixture of 9.2 g (29 mmol) of $H_2O_2$-urea adduct (30% $H_2O_2$) and 70 ml of ethanol, a solution of 12.5 g (29 mmol) of sulfide [compound 105 prepared according to Example 5] in 25 ml of ethanol is added. The reaction mixture is stirred for 4 hours at 40° C. Addition of 50 ml of distilled water, evaporation of the ethanol, addition of ethyl acetate and washing with sodium pyrosulfite solution and distilled water and standard work-up of the organic phases as outlined in Example 1 yields 11.6 g (89%) of compound 205 as a brown resin. Purification by flash chromatography on silica with ethyl acetate/hexane 1:1 gives 8.5 g of an off-white resin. MS (Cl): 443 (MH$^+$).

EXAMPLE 18

Preparation of Compound 206 (Table 2)

a) To a mixture of 10.1 g (32 mmol) of $H_2O_2$-urea adduct (30% $H_2O_2$) and 70 ml of ethanol, a solution of 12.5 g (29 mmol) of sulfide [compound 106 prepared according to Example 6] in 25 ml ethanol is added. The reaction mixture is stirred for 4 hours at 40° C. Addition of 50 ml of distilled water, evaporation of the ethanol, addition of ethyl acetate and washing with sodium pyrosulfite solution and distilled water and standard work-up of the organic phases as outlined in Example 1 yields 13.9 g (87%) of compound 206 as a brown resin. MS (Cl): 498 (M$^+$).

b) 30.0 g (62 mmol) of sulfide [compound 106 prepared according to Example 6], 31 ml of acetone and 12.1 g (124 mmol) of aqueous $H_2O_2$ (35% $H_2O_2$) are mixed at 25° C. The reaction mixture is heated for 6 hours at 45° C. Then 100 ml of distilled water and 150 ml of ethyl acetate are added. The organic phase is separated, washed with water and sodium pyrosulfite solution, dried over sodium sulfate and evaporated to yield 31.1 g (100%) of compound 206 as a brown resin. MS (Cl): 498 ($M^+$).

c) 30.0 g (62 mmol) of sulfide [compound 106 prepared according to Example 6], 31 ml of 2-butanone and 12.1 g (124 mmol) of aqueous $H_2O_2$ (35% $H_2O_2$) are mixed at 25° C. The reaction mixture is heated for 4 hours at 45° C. Then 100 m of distilled water and 150 ml of ethyl acetate are added. The organic phase is separated, washed with water and sodium pyrosulfite solution, dried over sodium sulfate and evaporated to yield 31.1 g (100%) of compound 206 as a black solid. MS (Cl): 498 ($M^+$). The product can be further purified by column chromatography on $SiO_2$ (eluent hexane/ethyl acetate 1:1). The resulting brown powder has a melting point of 94° C.

EXAMPLE 19

Preparation of Compound 208 (Table 2)

To a mixture of 7.3 g (23 mmol) of $H_2O_2$-urea adduct (30% $H_2O_2$) and 70 ml of ethanol, a solution of 12.5 g (29 mmol) of sulfide [compound 108 prepared according to Example 8] is added and the mixture is stirred for 4 hours at 40° C. Addition of 50 ml of distilled water, evaporation of the ethanol, addition of ethyl acetate and washing with sodium pyrosulfite solution and distilled water and standard work-up of the organic phases as outlined in Example 1 yields 11.6 g (89%) of compound 208 as a brown resin. Purification by flash chromatography on silica with ethyl acetate/hexane 1:1 gives 8.5 g of an off-white resin. MS (Cl): 499 ($MH^+$).

In analogy to Example 19 compounds 202, 209, 210, 211, 212, 213, 214, 215, 216 and 217 are prepared from the corresponding sulfides (compounds 102, 109, 110, 111, 112, 113, 114, 115, 116 and 117).

EXAMPLE 20

Preparation of Compound 301 (Table 3)

18.08 g (80 mmol) of N-isopropyl-4-phenylaminoaniline, 27.0 g (184 mmol) of n-octanethiol, 13.8 ml (184 mmol) of formaldehyde (36.5%), 40 ml of ethanol and 15.2 g (184 mmol) of concentrated HCl are mixed and then stirred for 3 hours at 15° C. The reaction mixture is then heated under reflux for 4 hours. After cooling, the reaction mixture is brought to pH 9 with 10% sodium hydroxide solution. Extraction with ethyl acetate and standard work-up of the organic phases as outlined in Example 1 yields 43.9 g (98%) of compound 301 as a dark oil. The crude product is further purified by flash chromatography on silica using a mixture of ethyl acetate and hexane as eluent to give 7 g (16%) of compound 301 as a brown oil. $^1H$- and $^{13}C$-NMR-spectra and elemental analysis are in good agreement with compound 301. MS (Cl): 543 ($MH^+$).

In analogy to Example 20, compounds 302-317 can be prepared from the corresponding amines and thiols as disclosed in the preparation of the compounds 102-117.

EXAMPLE 21

Preparation of a Mixture of Compounds 106 (Table 1) and 306 (Table 3)

To a mixture of 21.5 g (80 mmol) of N-(4-methyl-2-pentyl)-4-phenylaminoaniline, 40 ml of 1,4-dioxane, 9.0 g (92 mmol) of concentrated sulfuric acid and 21 ml of distilled water, a mixture of 18.6 g (92 mmol) of n-dodecanethiol and 6.9 ml (92 mmol) of formaldehyde (36.5%) is added at 25° C. The reaction mixture is then heated under reflux for 2 hours. After cooling a mixture of 8.1 g (40 mmol) of n-dodecanethiol and 3.0 ml (40 mmol) of formaldehyde (36.5%) is added at 25° C. The reaction mixture is again heated under reflux for 3 hours. After cooling, the reaction mixture is brought to pH 9 with 10% sodium hydroxide solution. Extraction with hexane and standard work-up of the organic phases as outlined in Example 1 yields after isolation and drying 45.3 g of a dark oil. Analysis by HPLC and GLC shows the following composition: 75.7% of compound 106 and 15.0% of compound 306 (HPLC); the amount of starting amine [N-(4-methyl-2-pentyl)-4-phenylaminoaniline] is less than 0.1% (GLC).

EXAMPLE 22

Stabilization of Black Vulcanizate 40.0 parts by weight of Buna CB 10® [polybutadiene, BAYER] are processed on mixing rolls at 60° C. with 60.0 parts by weight of natural rubber and 55.0 parts by weight of carbon black (N 330), 6.0 parts by weight of Ingralen 450® [extender oil], 5.0 parts by weight of zinc oxide [vulcanization activator], 2.0 parts by weight of stearic acid [vulcanization activator], 0.2 parts by weight of IRGANOX 1520® [processing stabilizer, Ciba Specialty Chemicals], 2.0 parts by weight of sulfur [vulcanizer], 0.6 part by weight of Vulkacit MOZ® [vulcanization accelerator, BAYER] and the parts by weight of the stabilizer to be tested in accordance with Table 7, to give a homogeneous mixture, the vulcanization system [sulfur and Vulkacit MOZ®] not being added until the end of the mixing process. The mixture is vulcanized in electrical heating presses at 150° C. to T95 on the rheometer curves, to give elastomer sheets of 2 mm thickness, 21 cm length and 8.0 cm width. Sections of the 2 mm rubber sheets are placed on a white cardboard underlay and stored in a circulating-air cabinet at 50° C. for 5 days. The contact surface or its margin is then evaluated visually for contact discoloration (staining): 0=no discoloration (or the discoloration of the reference in which no AO is present) and 5=greatest degree of discoloration. The slighter the contact discoloration, the better the stabilization. The results are given in Table 7.

TABLE 7

| Example | Stabilizer (amount in phr[c]) | Contact discoloration - visual |
|---|---|---|
| 22a[a] | — | 0 |
| 22b[a] | 2.0 phr of Vulkanox 4020 (RTM)[d] | 7 |
| 22c[a] | 4.0 phr of Vulkanox 4020 (RTM)[d] | >7 |
| 22d[a] | 3.6 phr of compound 106[e] | 6 |
| 22e[b] | 3.2 phr of compound 105[f] | 1 |

TABLE 7-continued

| | | |
|---|---|---|
| 22f[b)] | 3.2 phr of compound 105[g)] | 0.5 |
| 22g[b)] | 3.6 phr of compound 106[h)] | 0 |
| 22h[b)] | 3.6 phr of compound 106[i)] | 0.5 |
| 22i[b)] | 2.8 phr of compound 109 | 0 |
| 22k[b)] | 3.0 phr of compound 110 | 0 |
| 22l[b)] | 3.6 phr of compound 208 | 0 |
| 22m[b)] | 4.0 phr of compound 301 | 0 |
| 22n[b)] | 3.6 phr of compound 106/306[j)] | 0 |

[a)]Comparative Examples.
[b)]Inventive Examples.
[c)]phr is parts per hundred parts of substrate.
[d)]Vulkanox 4020 (RTM) [Bayer] is
4-[1,3-dimethylbutyl]aminodiphenylamine of the formula A

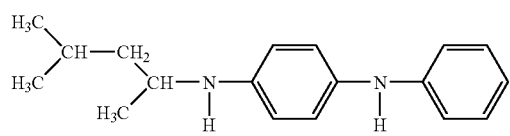

(A)

[e)]Compound 106 prepared according to U.S. Pat. No. 4,124,565
(Example I, Compound 7) [see Example 6b of the instant invention].
[f)]Compound 105 prepared according to Example 5a.
[g)]Compound 105 prepared according to Example 5b.
[h)]Compound 106 prepared according to Example 6a.
[i)]Compound 106 prepared according to Example 6c.
[j)]Mixture of compounds 106 and 306 prepared according to Example 21
[75.7% of compound 106 and 15.0% of compound 306].

EXAMPLE 23

Anti-fatigue Test

The Wallace-MRPRA fatigue tester is used. The fatigue tester measures the fatigue resistance of rubber under controlled conditions of test. Rubber ring specimens are mounted vertically on pulleys which are free to rotate. Each specimen is extended repeatedly at 300 cycles per minute to failure. The driving mechanism gives sinusoidal motion to the moving pulleys. The throw of the driving mechanism can be changed in steps, each representing 12.5% strain deformation between zero and 300% maximum. The position of the stationary specimen pulleys can be changed in steps each representing 12.5% strain deformation. A separate electrically operated counter is provided for each test specimen. The counters can read up to 999999 representing cycles×100. Each counter stops immediately the specimen it represents fails. Setting pre-strain and full strain: The pre-strain is set at 50%, the full strain at 150%.

Counting system: Each test station has its own counter and the counter will stop when its specimen fails. It follows that the counter will not operate if no specimen is in place. The counter is actuated by the force of the test specimen applies to the pulleys. The counter will not operate, or will operate intermittently if this force is less than 400 g. When all counters stop counting, the machine itself will stop automatically. It follows that the machine will not run if no specimens are in place. The test is carried out with NR/BR rubber ring specimens, a large number of cycles to failure mean a good fatigue resistance of the stabilized rubber, a small number a bad fatigue resistance.

The compounds of the formula I show excellent results in this anti-fatigue test comparable to the results obtained with Vulkanox 4020® [see footnote d) at the end of Table 7].

What is claimed is:

1. A process for preventing contact discoloration of substrates coming into contact with elastomers and stabilizing elastomers to prevent oxidative, thermal, dynamic, light -induced and/or ozone-induced degradation, which comprises incorporating into the elastomers, or applying to these, a mixture comprising
   a) at least a compound of formula I

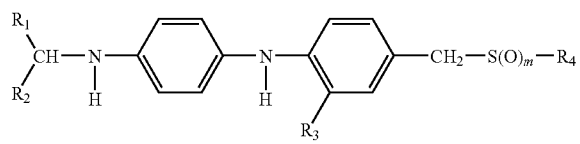

(I)

wherein
   $R_1$ is $C_1$-$C_{12}$alkyl,
   $R_2$ is $C_1$-$C_{12}$alkyl, or $R_1$ and $R_2$ together with the carbon atom to which they are attached form an unsubstituted or $C_1$-$C_4$alkyl substituted $C_5$-$C_{12}$cycloalkyl ring;
   $R_3$ is hydrogen,
   $R_4$ is an unsubstituted or cyano substituted $C_5$-$C_{18}$-alkyl; $C_7$-$C_9$phenylalkyl, unsubstituted or halogen, hydroxyl, cyano or $C_1$-$C_4$alkyl substituted phenyl or naphthyl; benzothiazolyl or —$R_6$—$CO_2$—$R_7$,
   $R_6$ is $C_1$-$C_{18}$alkylene,
   $R_7$ is $C_1$-$C_{18}$alkyl, and
   m is 0, 1 or 2; and
   b) at least a compound of formula I

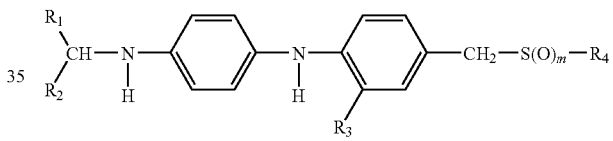

(I)

wherein
   $R_1$ is $C_1$-$C_{12}$alkyl,
   $R_2$ is $C_1$-$C_{12}$alkyl, or $R_1$ and $R_2$ together with the carbon atom to which they are attached form an unsubstituted or $C_1$-$C_4$alkyl substituted $C_5$-$C_{12}$cycloalkyl ring;
   $R_3$ is —$CH_2$—$S(O)_m$—$R_5$,
   $R_4$ and $R_5$ independently of each other are unsubstituted or cyano substituted $C_5$-$C_{18}$alkyl; $C_7$-$C_9$phenylalkyl, unsubstituted or halogen, hydroxyl, cyano or $C_1$-$C_4$alkyl substituted phenyl or naphthyl; benzothiazolyl or —$R_6$—$CO_2$—$R_7$,
   $R_6$ is $C_1$-$C_{18}$alkylene,
   $R_7$ is $C_1$-$C_{18}$alkyl, and
   m is 0, 1 or 2.

2. A process according to claim 1, wherein
   $R_1$ is $C_1$-$C_8$alkyl,
   $R_2$ is $C_1$-$C_8$alkyl, or $R_1$ and $R_2$ together with the carbon atom to which they are attached form an unsubstituted or $C_1$-$C_4$alkyl substituted $C_5$-$C_7$cycloalkyl ring;
   $R_4$ and $R_5$ independently of each other are unsubstituted or cyano substituted $C_5$-$C_{12}$-alkyl;
   $C_7$-$C_9$phenylalkyl, unsubstituted or halogen, cyano or $C_1$-$C_4$alkyl substituted phenyl or naphthyl; or —$R_6$—$CO_2$—$R_7$,
   $R_6$ is $C_1$-$C_{12}$alkylene,
   $R_7$ is $C_1$-$C_{12}$alkyl, and
   m is 0, 1 or 2.

3. A process according to claim 1, wherein
$R_4$ and $R_5$ independently of each other are $C_8$-$C_{12}$alkyl; benzyl, phenyl or —$R_6$—$CO_2$—$R_7$,
$R_6$ is $C_1$-$C_3$alkylene,
$R_7$ is $C_1$-$C_4$alkyl, and
m is 0, 1 or 2.

4. A process according to claim 1, wherein
$R_1$ is $C_3$-$0_5$alkyl,
$R_2$ is $C_1$-$C_3$alkyl, or $R_1$ and $R_2$ together with the carbon atom to which they are attached form a cyclohexyl ring;
$R_4$ and $R_5$ independently of each other are $C_8$-$C_{12}$alkyl; benzyl, phenyl or —$R_6$—$CO_2$—$R_7$,
$R_6$ is $C_1$-$C_3$alkylene,
$R_7$ is $C_1$-$C_4$alkyl, and
m is 0, 1 or 2.

5. A process according to claim 1, wherein the elastomer is a natural or synthetic rubber or blend thereof or vulcanizate prepared therefrom.

6. A process according to claim 1, wherein the elastomer is a vulcanized polymer of conjugated dienes, a halogen-containing polydiene vulcanizate, a polydiene copolymer vulcanizate or an ethylene-propylene terpolymer vulcanizate.

7. A process according to claim 1, wherein the compounds of formula I are incorporated or applied in an amount of 0.01 to 10% based on the weight of the elastomer.

8. A process according to claim 1, comprising incorporating or applying further additives.

9. A process according to claim 8 wherein the further additives are one or more components selected from the group consisting of pigments, dyes, fillers, levelling assistants, dispersants, plasticizers, vulcanization activators, vulcanization accelerators, vulcanizers, charge control agents, adhesion promoters, antioxidants and light stabilizers.

10. A process according to claim 8 wherein the further additives are selected from the group consisting of phenolic antioxidants, aminic antioxidants, organic phosphites or phosphonites, thio-synergists and benzofuranones.

11. A mixture comprising
a) at least a compound of the formula I

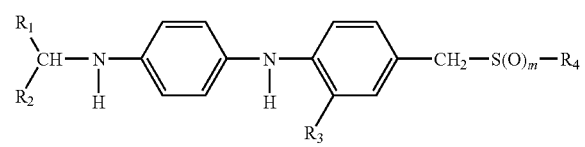

wherein
$R_1$ is $C_1$-$C_{12}$alkyl,
$R_2$ is $C_1$-$C_{12}$alkyl, or $R_1$ and $R_2$ together with the carbon atom to which they are attached form an unsubstituted or $C_1$-$C_4$alkyl substituted $C_5$-$C_{12}$cycloalkyl ring;
$R_3$ is hydrogen,
$R_4$ is an unsubstituted or cyano substituted $C_5$-$C_{18}$alkyl; $C_7$-$C_9$phenylalkyl, unsubstituted or halogen, hydroxyl, cyano or $C_1$-$C_4$alkyl substituted phenyl or naphthyl; benzothiazolyl or —$R_6$—$CO_2$—$R_7$,
$R_6$ is $C_1$-$C_{18}$alkylene,
$R_7$ is $C_1$-$C_{18}$alkyl, and
m is 0, 1 or 2; and b) at least a compound of the formula I

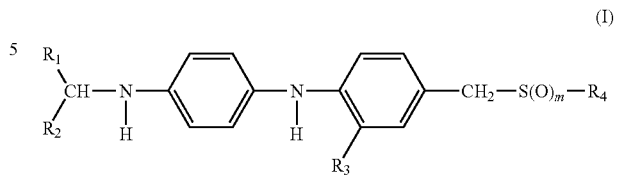

wherein
$R_1$ is $C_1$-$C_{12}$alkyl,
$R_2$ is $C_1$-$C_{12}$alkyl, or $R_1$ and $R_2$ together with the carbon atom to which they are attached form an unsubstituted or $C_1$-$C_4$alkyl substituted $C_5$-$C_{12}$cycloalkyl ring;
$R_3$ is —$CH_2$—$S(O)_m$—$R_5$,
$R_4$ and $R_5$ independently of each other are unsubstituted or cyano substituted $C_5$-$C_{18}$alkyl; $C_7$-$C_9$phenylalkyl, unsubstituted or halogen, hydroxyl, cyano or $C_1$-$C_4$alkyl substituted phenyl or naphthyl; benzothiazolyl or —$R_6$—$CO_2$—$R_7$,
$R_6$ is $C_1$-$C_{18}$alkylene,
$R_7$ is $C_1$-$C_{18}$alkyl, and
m is 0, 1 or 2.

12. A composition comprising
a) an elastomer susceptible to oxidative, thermal, dynamic, light-induced and/or ozone-induced degradation, and
b) as stabilizer, a mixture according to claim 11.

13. A compostion according to claim 12, comprising in addition to components (a) and (b), further additives.

14. A compound of the formula I

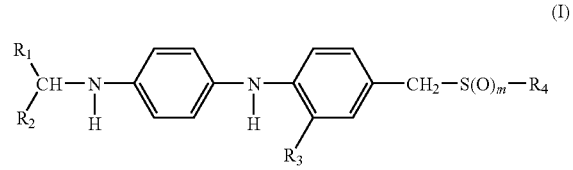

wherein
$R_1$ is $C_1$-$C_{12}$alkyl,
$R_2$ is $C_1$-$C_{12}$alkyl, or $R_1$ and $R_2$ together with the carbon atom to which they are attached form an unsubstituted or $C_1$-$C_4$alkyl substituted $C_5$-$C_{12}$cycloalkyl ring;
$R_3$ is —$CH_2$—$S(O)_m$—$R_5$,
$R_4$ and $R_5$ independently of each other are unsubstituted or cyano substituted $C_5$-$C_{18}$-alkyl;
$C_7$-$C_9$phenylalkyl, unsubstituted or halogen, hydroxyl, cyano or $C_1$-$C_4$alkyl substituted phenyl or naphthyl; benzothiazolyl or —$R_6$—$CO_2$—$R_7$,
$R_6$ is $C_1$-$C_{18}$alkylene,
$R_7$ is $C_1$-$C_{18}$alkyl, and
m is 0, 1 or 2.

15. A composition comprising
a) an elastomer susceptible to oxidative, thermal, dynamic, light-induced and/or ozone-induced degradation, and
b) as stabilizer, a compound of the formula I according to claim 14.

* * * * *